US00PP12386P2

(12) United States Plant Patent
Utecht

(10) Patent No.: US PP12,386 P2
(45) Date of Patent: Feb. 5, 2002

(54) GERANIUM PLANT NAMED 'FISBLIZROSE'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/772,844

(22) Filed: Jan. 31, 2001

(51) Int. Cl.[7] ..... A01H 5/00
(52) U.S. Cl. ..... Plt./332
(58) Field of Search ..... Plt./332, 324

(56) References Cited

PUBLICATIONS

2001 Fischer Schmüllung Plant Alliance Catalogue featuring 'Fisblizrose' on p. 23.
German Plant Application and Denomination—'Fisblizrose' (Dec. 15, 1998).
Official Gazette of the Community Plant Variety Office, European Community Application—'Fisblizrose' (Dec. 15, 1999).
Canadian Application, Denomination, Plant Varieties Journal No. 38, Canada 2001, pp. 59–60.
GTITM UPOVROM Citation for 'Fisblizrose' as per QZ PBR 991463; Oct. 20, 1999.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisblizrose', as described and illustrated, and particularly characterized by the combined features of pink, single-type flowers, medium-green, zoned foliage, and with tall, trailing, though well-branched and bushy, plant habit.

1 Drawing Sheet

BACKGROUND OF THE INVENTION

The present invention comprises a new and distinct cultivar of geranium, botanically known as *Pelargonium peltatum*, and hereinafter referred to by the cultivar name 'Fisblizrose'.

'Fisblizrose' is a product of a planned breeding program which had the objective of creating new ivy geranium cultivars with single-type flowers, relatively vigorous, but well-branched growth habit, and various flower colors. 'Fisblizrose' originated from a hybridization made by the inventor Angelika Utecht in a controlled breeding program in Galdar, Gran Canaria, Spain, in 1996.

The female parent was a hybrid seedling no. K95-823-39 (unpatented), derived from a cross between the seedling K92-1652-1 (unpatented) and 'Fisrock', U.S. Plant Pat. No. 10,365, and characterized by deep red single-type flowers, medium-green, zoned foliage, and medium to tall plant habit. The male parent of 'Fisblizrose' was seedling no. 300-2 (unpatented), originated from self-pollinating the commercial variety 'Amiral Bouvet' (unpatented) having salmon-red, semi-double flowers and moderately vigorous growth.

'Fisblizrose' was selected as one flowering plant within the progeny of the stated cross by Angelika Utecht in a controlled environment in Galdar, Gran Canaria, Spain, in 1997. The first act of asexual reproduction of 'Fisblizrose' was accomplished when vegetative cuttings were taken from the initial selection in the fall of 1997 in a controlled environment in Galdar, Gran Canaria, Spain, by, or under the supervision of, Angelika Utecht. Horticultural examination of plants grown from these cuttings initiated in the spring of 1998. in Hillscheid, Germany, and continuing thereafter, has demonstrated that the combination of characteristics as herein disclosed for 'Fisblizrose' are firmly fixed and are retained through successive generations of asexual reproduction.

'Fisblizrose' has not been observed under all possible environmental conditions. The phenotype may vary significantly with variations in environment such as temperature, light intensity and day length.

BRIEF DESCRIPTION OF THE INVENTION

The following observations, measurements, and comparisons describe plants grown in Hillscheid, Germany, and in Langley, British Columbia, Canada, under greenhouse conditions which approximate those generally used in commercial practice.

The following traits have been repeatedly observed and are determined to be basic characteristics of 'Fisblizrose', which in combination distinguish this geranium as a new and distinct cultivar:

1. Intense pink, single-type flowers;

2. Numerous inflorescences, well above the foliage;

3. Ivy-shaped, medium-green, distinctly zoned foliage;

4. Fairly vigorous, though well-branched and bushy, growth habit; and

5. Early to medium spring flowering response.

Of the many commercial cultivars known to the present inventor, the most similar is the variety 'Fispink', U.S. Plant Pat. No. 9,920. In comparison to 'Fispink', 'Fisblizrose' has a less bluish, sweeter tone of pink flower color, with weaker markings on petals, and rounder florets with somewhat wider upper petals. Furthermore 'Fisblizrose' has a slightly lighter foliage color, with distinct zonation, in contrast to 'Fispink' (without zonation), and with taller plant habit.

BRIEF DESCRIPTION OF THE DRAWING

The accompanying photographic drawing shows typical flower and foliage characteristics of 'Fisblizrose' with colors being as true as possible with an illustration of this type. The photograph shows 3 plants growing in a hanging-basket.

The measurements were taken in Langley, Canada, on Jul. 20, 2000. The plants were growing in 6 inch pots in a greenhouse, and had had 15 weeks of cultivation time from the planting of rooted cuttings on April 3. The plants had not been pinched.

In the following description color references are made to The Royal Horticultural Society Colour Chart (R.H.S.). The color values were determined indoors from plants developed in a greenhouse in May, 2000, in Hillscheid, Germany.

Classification:

*Botanical.*—A hybrid of the species *Pelargonium peltatum* L'Hérit. ex Aiton.

*Commercial.*—Ivy-leafed geranium, cv. 'Fisblizrose'.

Inflorescence:

*Umbel.*—Shape: Roughly semi-spherically, but loose and somewhat irregular. Average diameter: 110 mm. Average depth: 52 mm. Peduncle length: 155 mm. Peduncle color: Light green, RHS 143 A. Pedicel length: 29 mm, with spur. Pedicel color: Green, RHS 143 B. Number of flowers per umbel: Approximately 6 to 8. Lastingness of the umbel: Approximately 15 days at 18° C.

*Corolla.*—Average diameter: 47 mm. Form: Single. Shape: Nearly round. Number of petals: 5. Petal size: Upper petals are 29–31 mm in length, 18–20 mm in width; lower petals are 27–29 mm in length, 19–21 mm in width. Petal shape: Upper petals are spatulate to narrow obovate, lower petals are obovate, attenuate base, margin entire. Color (general tonality from a distance of three meters): Bright pink. Color of upper petals: RHS 58 B. Markings of upper petals: Two red veins at the base RHS 53 B. Color of lower petals: RHS 58 C. Color of lower surface of petals: RHS 52 C. Color of sepals: Mainly green, RHS 137 D, upper sepal with slight infusion of anthocyanin RHS 47 A on outer surface, RHS 48 A on inner surface. Number of sepals: 5. Sepal size: 13–15 mm in length, 4 mm in width for the largest, upper sepal, 3 mm in width for the other sepals. Sepal shape: Linear to lanceolate, acute tip, base truncate, surface with thin pubescence, margin entire.

*Bud: (just prior to petals unfolding).*—Shape: Narrow elliptic. Sepal Color (lower part): Green, RHS 137 D. Petal Color (upper part): Salmon, near RHS 43 B. Length: 19 mm. Width: 7 mm.

*Reproductive organs.*—Androecium: 7 fertile anthers, with whitish filaments, orange pollen, RHS 30 A, plentiful pollen production. Gynoecium: Whitish style, and reddish, 5–6 lobed stigma, one pistil per flower. Fertility/Seed set: Weak seed set during the summer not affecting development of new flowers, moderate seed set through late summer to fall. Seed: Oblong, 4–5 mm in length, brown RHS 177 B. Fruit: Oblong, approximately 6 mm in length; rostrate, rostrum 35–40 mm in length when ripe.

*Spring flowering response period.*—In Hillscheid, Germany, in 2000, plants had on average 1.7 flowers opened 12 weeks after planting of rooted cuttings (pinched plants).

*Outdoor flower production.*—Medium to rich flowering, the flower count in Hillscheid, Germany, indicated about 4 inflorescences per plant in mid May.

*Durability.*—Good rain resistance (typical for single flowered varieties), moderately shattering (not very strong for a single flowered variety).

*Stability of flower color.*—Fair, may slightly fade when maturing, RHS 66 D.

*Lastingness of the individual bloom.*—Approximately 6–7 days at 18° C.

*Fragrance.*—None.

Plant:

*Foliage.*—Shape: Ivy-shaped, with distinct lobes. Texture: Glossy and smooth. Margin: Entire, apart from the lobes. Base: Open to wide open, cordate. Apex: Rounded. Size of leaf: 81 mm wide, 45–50 mm long. Color of upper surface: Medium green, approximately RHS 137 B. Color of lower surface: Approximately RHS 137 D. Zonation: Brown, RHS 166 A, forming a small ring in the center of the leaf. Petioles: 40–50 mm long, 2–3 mm diameter, light green color approximately RHS 143 C.

*General appearance and form.*—Internode length: 40–50 mm. Branching pattern: 7.5 branches. Plant height: 59 cm as measured from the top of the soil (from the base of the main stem) to the tops of the branches(15 week old plants in Langley, Canada), 100 cm (in mid September in Hillscheid, Germany 31 weeks old).

Disease/pest resistance/susceptibility: None observed to date.

I claim:

1. A new and distinct cultivar of geranium plant named 'Fisblizrose', as described and illustrated.

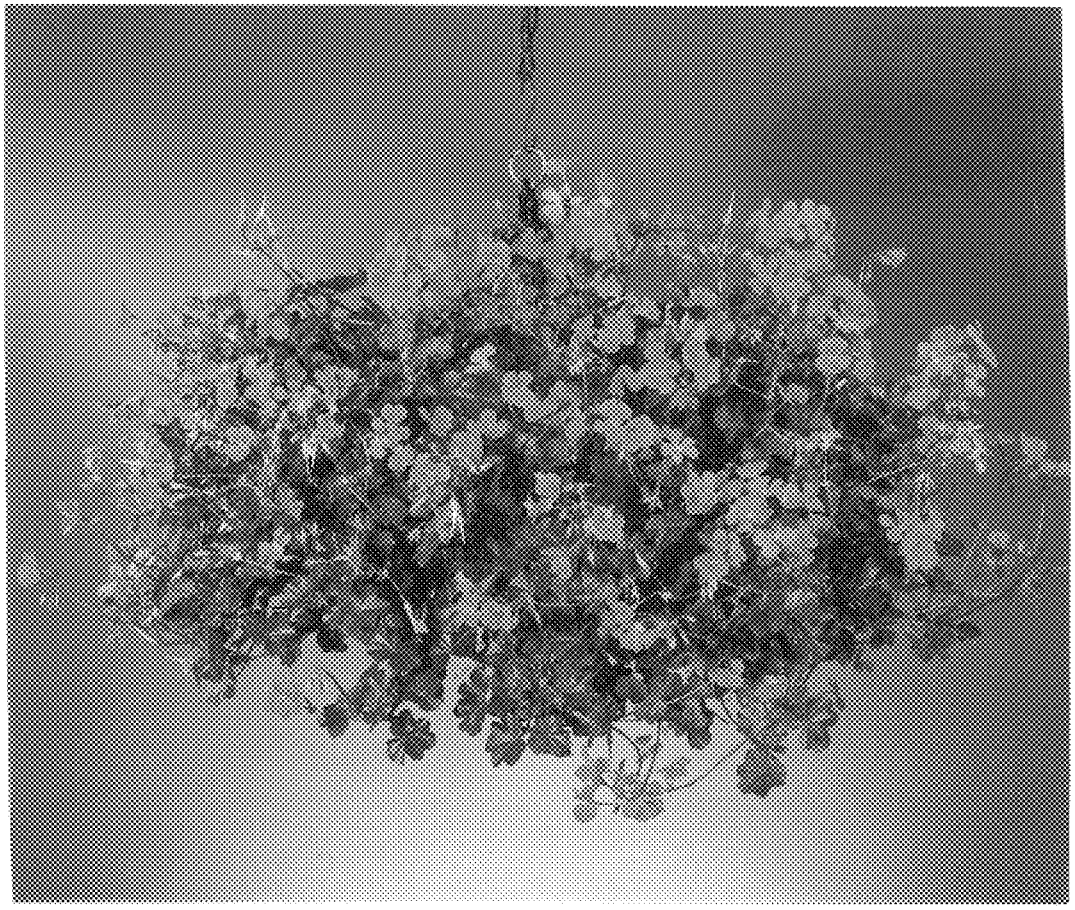

* * * * *